(12) United States Patent
Wada et al.

(10) Patent No.: US 9,370,307 B2
(45) Date of Patent: Jun. 21, 2016

(54) SUBJECT INFORMATION ACQUISITION DEVICE

(71) Applicant: CANON KABUSHIKI KAISHA, Tokyo (JP)

(72) Inventors: Yoshiko Wada, Kyoto (JP); Masakazu Toi, Kyoto (JP); Toshiyuki Kitai, Kishiwada (JP)

(73) Assignee: Canon Kabushiki Kaisha, Tokyo (JP)

( * ) Notice: Subject to any disclaimer, the term of this patent is extended or adjusted under 35 U.S.C. 154(b) by 72 days.

(21) Appl. No.: 13/629,287

(22) Filed: Sep. 27, 2012

(65) Prior Publication Data
US 2013/0085372 A1   Apr. 4, 2013

(30) Foreign Application Priority Data

Sep. 30, 2011   (WO) .................. PCT/JP2011/072577

(51) Int. Cl.
*A61B 5/05* (2006.01)
*A61B 5/00* (2006.01)
*G01S 15/89* (2006.01)
*G01S 7/52* (2006.01)

(52) U.S. Cl.
CPC ........... *A61B 5/0095* (2013.01); *G01S 7/52079* (2013.01); *G01S 15/8915* (2013.01); *G01S 15/8929* (2013.01)

(58) Field of Classification Search
CPC .................................................... A61B 5/0095
USPC ................................................... 600/407, 437
See application file for complete search history.

(56) References Cited

U.S. PATENT DOCUMENTS

| | | | |
|---|---|---|---|
| 7,295,928 B2* | 11/2007 | Hassan et al. | 702/9 |
| 2002/0035327 A1* | 3/2002 | Kruger | 600/437 |
| 2010/0174197 A1* | 7/2010 | Nakajima et al. | 600/478 |
| 2011/0230762 A1* | 9/2011 | Tokita et al. | 600/437 |

FOREIGN PATENT DOCUMENTS

| | | |
|---|---|---|
| DE | 10260667 A1 | 7/2004 |
| JP | 2009-082399 A | 4/2009 |
| JP | 2009-082402 A | 4/2009 |
| JP | 2009-119275 A | 6/2009 |
| JP | 2009-219656 A | 10/2009 |
| JP | 2010-167004 A | 8/2010 |
| JP | 2011-125406 A | 6/2011 |
| JP | 2011-125571 A | 6/2011 |
| JP | 2011-172730 A | 9/2011 |

* cited by examiner

*Primary Examiner* — Tse Chen
*Assistant Examiner* — Jason Ip
(74) *Attorney, Agent, or Firm* — Canon USA Inc., IP Division

(57) ABSTRACT

A subject information acquisition device includes a first holding member that holds a subject of a patient, a first probe that detects an acoustic wave having propagated through the first holding member and that performs a scanning operation, a first holding-member support located on a patient side from a scanning range of the first probe and that reduces bending of the first holding member, and a second probe located on the patient side from the scanning range of the first probe.

13 Claims, 6 Drawing Sheets

US 9,370,307 B2

SUBJECT INFORMATION ACQUISITION DEVICE

TECHNICAL FIELD

The present invention relates to a subject information acquisition device using an acoustic wave.

BACKGROUND ART

In the medical field, research is being actively pursued on optical imaging devices that irradiate a living body with light from a light source, such as a laser, and visualize information about the inside of the living body acquired based on the light that has entered. Photoacoustic imaging is one of these optical imaging technologies. In photoacoustic imaging, a living body is irradiated with pulsed light generated from a light source. Acoustic waves (typically ultrasonic waves) generated from biological tissues that have absorbed the energy of the pulsed light having propagated and diffused inside the living body are detected. Based on the detected signal, information about the inside of the living body is visualized. Specifically, by utilizing a difference in the light-energy absorption rate between a target part, such as a tumor, and the other tissues, an acoustic wave detector detects elastic waves generated when the target part instantaneously expands in response to absorption of the energy of the irradiated light. By mathematically and analytically processing this detected signal, a distribution of optical properties inside the living body or information related to the distribution of optical properties, particularly, a distribution of initial sound pressures, a distribution of optical energy absorption densities, and a distribution of optical absorption coefficients, and so forth, can be acquired.

In photoacoustic imaging, it is necessary to stably maintain the shape of a subject during measurement in order to acquire appropriate images. Thus, PTL 1 illustrated in FIG. 10 discloses a technique for stably maintaining the shape of a subject to acquire information about the subject. Specifically, PTL 1 discloses a technique for stably maintaining the shape of a subject by holding the subject between two press plates 2a and 2b, and for receiving acoustic waves by performing scanning with one acoustic wave receiver 5. In addition, in PTL 1, the press plate 2b is used as a scanning surface of the acoustic wave receiver 5.

CITATION LIST

Patent Literature

PTL 1 Japanese Patent Laid-Open No. 2011-125571

As described above, in PTL 1, a subject is held by using holding members, such as press plates, whereby an appropriate image is acquired.

However, it is desired for subject information acquisition devices to acquire higher-quality images than those acquirable with PTL 1.

Accordingly, according to aspects of the present invention, a subject information acquisition device stably maintains the shape of a subject and acquires high-quality images.

SUMMARY OF INVENTION

According to an aspect of the present invention, a subject information acquisition device includes a first holding member arranged to hold a subject of a patient, a first probe configured to detect an acoustic wave having propagated through the first holding member and to perform a scanning operation, a first holding-member support located on a patient side from a scanning range of the first probe and configured to reduce bending of the first holding member, and a second probe located on the patient side from the scanning range of the first probe.

Further features of the present invention will become apparent from the following description of exemplary embodiments with reference to the attached drawings.

DESCRIPTION OF EMBODIMENTS

In the technique disclosed in PTL 1, when the shape of a subject is maintained by using press plates serving as holding members, the holding members bend due to elasticity of the subject.

Figure 11:
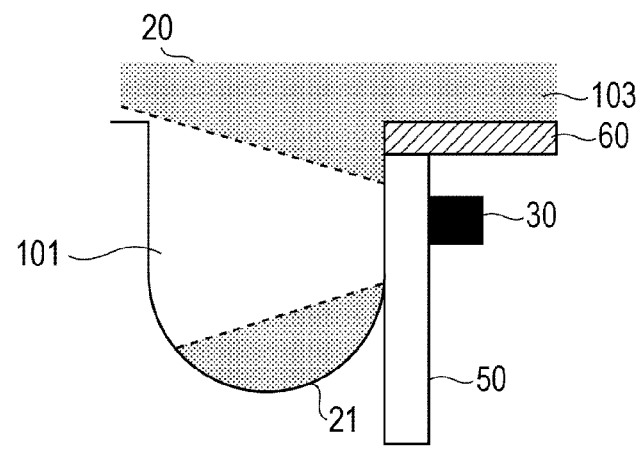
FIG. 11 is a schematic diagram of a subject information acquisition device including a holding-member support according to a comparative example.

Accordingly, as in a subject information acquisition device according to a comparative example illustrated in FIG. 11, a holding-member support 60 that reduces bending of a holding member 50 for maintaining the shape of a subject 21 may be placed on a patient-20 side of the holding member 50. The subject information acquisition device illustrated in FIG. 11 includes a scanning probe 30 configured to perform a scanning operation, the holding member 50, and the holding-member support 60. "Patient" indicates the whole living body, whereas "subject" indicates part (such as breast) of the living body, i.e., part to be examined. "Patient side" indicates a direction from the scanning probe 30 towards a non-subject part of the patient. For example, the "patient side" of the holding-member support 60 indicates, in FIG. 11, the direction above the holding-member support 60 on the paper.

The subject information acquisition device according to the comparative example illustrated in FIG. 11 can visualize light absorbers existing in a first detection region 101, i.e., a region where the scanning probe 30 can detect acoustic waves. However, the holding-member support 60 limits the scanning range of the scanning probe 30, and thus there is a blind region 103, i.e., a region where the scanning probe 30 is unable to detect acoustic waves. That is, a limited range of the angle of view of the probe results in light absorbers existing in the blind region 103 not being visualized.

Accordingly, one aspect of the present invention provides a subject information acquisition device that includes a feature in which a probe other than a scanning probe is located on the patient side from the scanning range of the scanning probe.

Exemplary embodiments of the present invention will be described below with reference to the drawings. Similar components are generally assigned the same references and a description thereof will be omitted.

First Exemplary Embodiment

Figure 1:
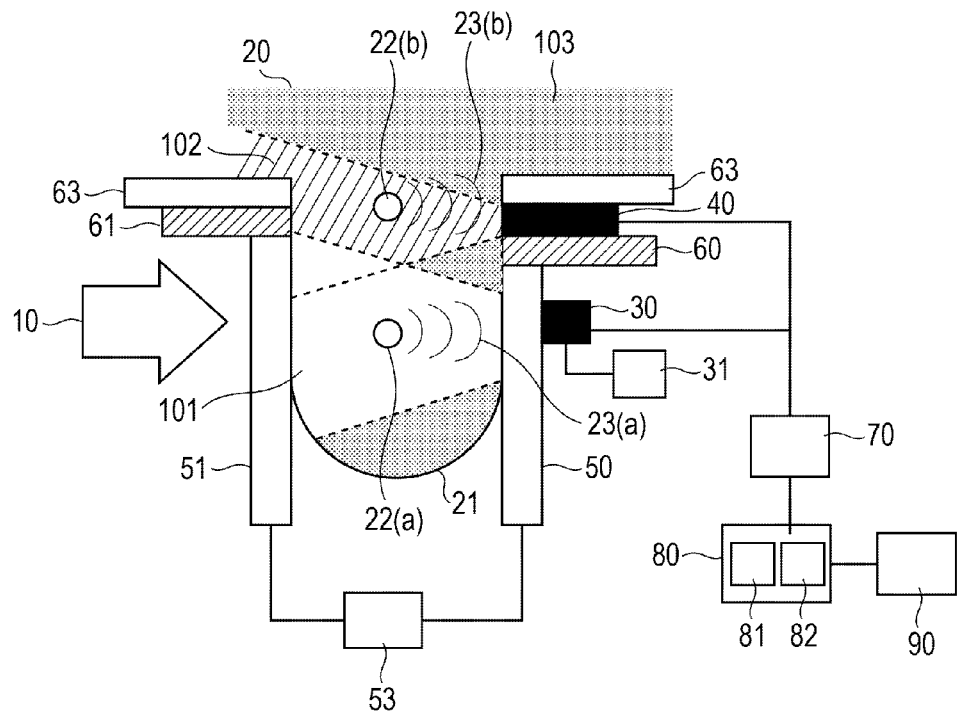
FIG. 1 is a schematic diagram of a subject information acquisition device according to a first exemplary embodiment.

FIG. 1 is a schematic diagram of a subject information acquisition device according to a first exemplary embodiment. The subject information acquisition device illustrated in FIG. 1 includes, as basic hardware components, a scanning probe 30 serving as a first probe configured to perform a scanning operation, a probe 40 serving as a second probe, a first holding member 50, a first holding-member support 60, and a signal processor 80. The subject information acquisition device further includes a second holding member 51 positioned so as to face the first holding member 50, and a second holding-member support 61. Here, each "probe" includes an acoustic wave detector that detects acoustic waves, a control unit of the acoustic wave detector, and a housing enclosing these components.

As illustrated in FIG. 1, in the subject information acquisition device according to this embodiment, the probe 40 is located on the patient side from the scanning range of the scanning probe 30 and above the scanning probe 30.

In this embodiment, a subject 21 is irradiated with light 10 emitted from a light source. Light absorbers 22(a) and 22(b) inside the subject 21 absorb the light 10, thereby generating acoustic waves 23(a) and 23(b). The scanning probe 30 detects the acoustic wave 23(a) generated at the light absorber 22(a) existing in a first detection region 101, via the holding member 50. In addition, the probe 40 detects the acoustic wave 23(b) generated at the light absorber 22(b) existing in a second detection region 102. The signal processor 80 then generates combined image data of image data corresponding to a signal detected by the scanning probe 30 and image data corresponding to a signal detected by the probe 40. The combined image data is displayed on a display device 90.

As described above, this embodiment includes a feature in which the probe 40 is located on the patient side from the scanning probe 30 and detects the acoustic wave 23(b) generated at the light absorber 22(b) existing in the second detection region 102. This enables visualization of a region that is unable to be visualized with a configuration in which acoustic waves are detected only with the scanning probe 30.

In this embodiment, a pressing mechanism 53 moves the first holding member 50 and the second holding member 51 to hold the subject 21 therebetween, whereby the shape of the subject 21 is maintained. In this manner, the thickness of the subject can be reduced, and thus light is likely to reach a light absorber at a deep part of the subject. It is not necessary to hold the subject from both sides as long as the shape of the subject can be maintained only with the first holding member 50. That is, the subject information acquisition device need not include the second holding member 51, the second holding-member support 61, and the pressing mechanism 53.

Also in the subject information acquisition device according to this embodiment, a patient support 63 that supports a patient 20 is located between the patient 20 and the probe 40. However, subject information acquisition devices of certain types, such as standing and seated types, need not include the patient support 63 because the applied weight of the patient is small.

In addition, a detection surface of the probe 40 may be appropriately set in a desirable direction for detecting acoustic waves.

Moreover, when acoustic impedance matching is desired between the subject 21 and another member, an acoustic matching material, such as ultrasound gel, water, or mineral oil, may be used.

Subject information acquisition methods performed by the signal processor 80 will be described below. Numerals below match numerals of processes illustrated in FIGS. 2 and 3.

First, the subject information acquisition method illustrated in FIG. 2 will be described.

Process 1 (S111, S112): Process of Detecting Acoustic Waves with probes and acquiring electrical signals In this process, the subject 21 is irradiated with the light 10, and the scanning probe 30 and the probe 40 detect the acoustic waves 23(a) and 23(b) generated at the light absorbers 22(a) and 22(b) in the subject to acquire electrical signals. At this time, the scanning probe 30 detects the acoustic wave 23(a) generated at the light absorber 22(a) existing in the first detection region 101, via the holding member 50. Also, the probe 40 detects the acoustic wave 23(b) generated at the light absorber 22(b) existing in the second detection region 102.

At this time, the acoustic waves can be detected with the scanning probe 30 and the probe 40 by irradiating the entire subject 21 with light.

Alternatively, the first detection region 101 and the second detection region 102 may be separately irradiated with light and the probes corresponding to the regions may detect acoustic waves generated in the regions. Accordingly, even if an insufficient amount of light is radiated to a wide range at one time, sufficient amounts of light can be ensured in the regions when the regions are separately irradiated with light. At this time, the order in which the regions are irradiated with light does not matter. Also, the regions may be individually irradiated with light at the same time.

Process 2 (S121): Process of Converting Electrical Signals into Digital Signals

In this process, a signal collector 70 amplifies the electrical signals acquired in S111 and S112, and converts the electrical signals into digital signals. In addition, the digital signal is recorded in a memory of the signal processor 80 in association with the position of an element that has acquired the digital signal.

When detection is performed at the same position a plurality of times, signals detected at the same position may be simply added as well as averaged after completion of the detection.

In the case of an element not working properly or a probe with a sparse array, a missing signal corresponding to the position may be interpolated by newly creating a signal based on the signals from surrounding positions. For example, the missing signal may be interpolated by averaging signals from elements adjacent to the position without the detection element, or the missing signal may be interpolated by shifting an original signal in the time domain taking into account the phase to perform averaging and create a pseudo-signal.

This process can be omitted when the following process is performed on the electrical signals, i.e., analog signals.

Process 3 (S131): Process of Combining Detected Signals

In this process, the signal processor 80 combines detected signals. Here, the detected signals are concepts including the electrical signals acquired in S111 and S112 and the digital signals acquired in S121.

At this time, when there is a signal transmission medium, such as the first holding member 50, between the scanning probe 30 or the probe 40 and the subject 21, and the speed of the sound propagating in the subject 21 differs from that in the signal transmission medium, the detected signals are combined taking into account the signal acquisition timing lag due to the signal transmission medium. For example, in one case, the first holding member 50 is located between the scanning probe 30 and the subject 21 while the probe 40 is directly in contact with the subject 21. In this case, prior to combining, the signal from the probe 40 is delayed, assuming that the first holding member 50 is located between the probe 40 and the subject 21. Alternatively, a signal obtained by taking into account the first holding member 50 is removed from the signal of the scanning probe 30 before the detected signals are combined.

When the probes have different element widths or center frequencies, the detected signals may be combined, taking into account the characteristics of the probes, such as the element widths and the directivities.

When a signal corresponding to a specific position is missing in the combined signal, the missing signal may be interpolated by newly creating a signal based on the signals from the probes. For example, the missing signal can be interpolated by averaging signals from elements adjacent to the position without the element or by shifting an original signal in the time domain taking into account the phase to perform averaging and create a pseudo-signal.

Process 4 (S141): Process of Generating Image Data from Combined Detected Signal In this process, the signal processor 80 performs image reconstruction based on the combined detected signal generated in S131 to generate image data of the inside of the subject. In this process, since image reconstruction is performed based on the combined detected signal, combined image data of image data corresponding to the signal detected by the scanning probe 30 and image data corresponding to the signal detected by the probe 40 can be generated. Here, the image data represents a distribution of optical properties inside the subject or information related to the distribution of optical properties, particularly, a distribution of initial sound pressures, a distribution of optical energy absorption densities, a distribution of absorption coefficients, and so forth.

Next, the subject information acquisition method illustrated in FIG. 3 will be described. Processes similar to those in FIG. 2 are assigned the same processing numerals and a detailed description thereof will be omitted.

Figure 2:
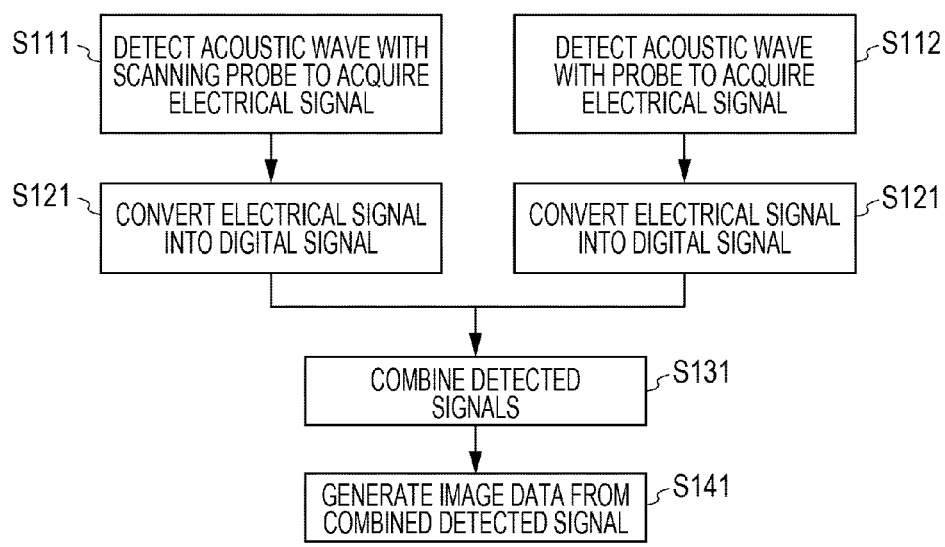
FIG. 2 is a diagram illustrating a processing flow of a subject information acquisition method according to the first exemplary embodiment.
Figure 3:
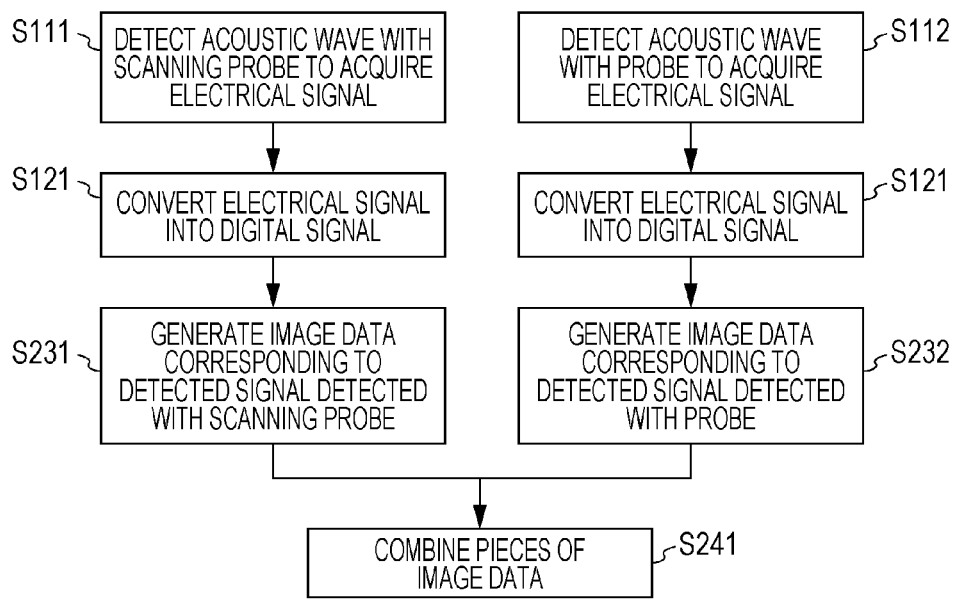
FIG. 3 is a diagram illustrating another processing flow of the subject information acquisition method according to the first exemplary embodiment.

The subject information acquisition method illustrated in FIG. 3 differs from the subject information acquisition method illustrated in FIG. 2 in that pieces of image data for the scanning probe 30 and the probe 40 are generated based on the detected signals obtained by the respective probes and then the pieces of image data are combined.

Process 3 (S231, S232): Process of Generating Pieces of Image Data Corresponding to Detected Signals In this process, the signal processor 80 generates image data corresponding to a signal detected by the scanning probe 30 and image data corresponding to a signal detected by the probe 40 based on the respective detected signals. At this time, image reconstruction is performed, taking into account the characteristics of the probes, such as the element width and the directivity, and the characteristics of the holding member.

Process 4 (S241): Process of Combining Pieces of Image Data

In this process, the signal processor 80 combines the image data, generated in S231, corresponding to the signal detected by the scanning probe 30 and the image data, generated in S232, corresponding to the signal detected by the probe 40. At this time, the signal processor 80 can combine the pieces of image data, taking into account the capturing positions and voxel sizes of two images, the sizes of the elements, the directivities, and the center frequencies. A case of probes having different center frequencies will be described below.

In general, an image acquired with a probe having a high center frequency has a high resolution in a direction perpendicular to the detection surface of the probe. That is, since images obtained with probes having different center frequencies have different resolutions, an image obtained by simply combining these images is unnatural.

Accordingly, the images are combined after converting the resolution of the image acquired with the probe having the higher center frequency to match the resolution of the image acquired with the probe having the lower center frequency. In this way, unnaturalness of the combined image is reduced. Examples of the resolution matching method include, but are not limited to, averaging absorption coefficients in directions perpendicular to the detection surfaces of the probes or applying a filer.

The subject information acquisition methods illustrated in FIGS. 2 and 3 can also be similarly performed in subject information acquisition devices according to embodiments described below.

Components of the subject information acquisition device will be described below.

(Light Source)

As the light source, a pulsed light source capable of generating light pulses of the order of several to several hundred nanoseconds may be used. Specifically, a pulse width of approximately 10 nanoseconds is used to efficiently generate acoustic waves. While a laser may be used to obtain a high output, a light-emitting diode or the like may also be used instead of the laser. Various types of lasers, such as a solid-state laser, a gas laser, a dye laser, or a semiconductor laser may be used. Timing, waveform, and intensity of radiation are controlled by a light-source control unit (not illustrated). In addition, the light source may be capable of performing scanning so as to irradiate a wide range of the subject 21 with light. Also, the light source may be integrally provided in the subject information acquisition device or separately provided as another device. Furthermore, a plurality of light sources for respective probes may be provided in order to irradiate respective detection regions of the scanning probe 30 and the probe 40 with light. Moreover, a combination of an optical fiber, an optical lens, and a prism can be used as an optical system from the light source to the radiation surface of the subject 21.

(Scanning Probe 30)

The scanning probe 30 performs scanning along the first holding member 50 by a scanning mechanism 31. This scanning mechanism 31 is controlled by a scanning control unit (not illustrated). The scanning probe 30 includes an acoustic wave detector in which a plurality of detection elements for detecting acoustic waves, such as piezoelectric elements, are arranged in an in-plane direction, a control unit of the acoustic wave detector, and a housing. The scanning probe 30 can acquire signals at a plurality of positions at one time. Scanning may be performed by the scanning probe 30 in synchronization with the light-emitting timing of the light source.

(Probe 40)

The probe 40 includes an acoustic wave detector in which a plurality of detection elements for detecting acoustic waves, such as piezoelectric elements, are arranged in an in-plane direction, a control unit of the acoustic wave detector, and a housing. The probe 40 can acquire signals at a plurality of positions at one time.

Figure 4A:
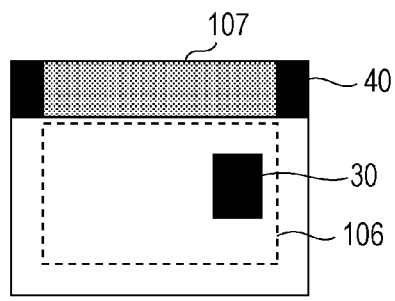
FIG. 4A is a diagram illustrating an example of arrangement of a probe according to the first exemplary embodiment.
Figure 4B:
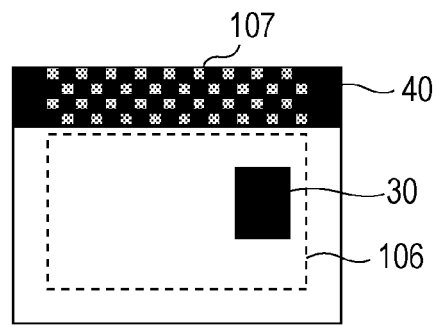
FIG. 4B is a diagram illustrating an example of arrangement of the probe according to the first exemplary embodiment.

As an example, a representative element arrangement in which the probe 40 is located above the scanning probe 30 will be described using FIGS. 4A and 4B. FIGS. 4A and 4B are diagrams of the probe 40 viewed from the subject through the first holding member 50. As illustrated in FIG. 4A, an element region 107, i.e., the acoustic wave detector of the probe 40, has a width substantially equal to a scanning range 106 of the scanning probe 30. However, since the scanning range 106 of the scanning probe 30 is wide, the number of elements of the probe 40 increases and consequently processing time increases. Accordingly, in order to shorten the processing time when the probe 40 has a large element arrangement width, the number of elements to perform processing may be reduced by selecting elements to operate. The method for selecting elements to operate includes switching between ON/OFF of operations of elements by means of a detection circuit or switch. In addition, a sparse array type may be used as the acoustic wave detector of the probe 40 as illustrated in FIG. 4B in order to shorten the processing time. Such element arrangement can also be similarly adopted in cases other than the case in which the probe 40 is disposed above the scanning probe 30.

When the light source moves along with the scanning probe 30, positions of elements to operate of the probe 40 may be selected in accordance with a position from which light is radiated to the subject. Similarly, when a light source used by the probe 40 moves, elements for a position from which light is radiated are selectively operated to perform detection.

The probe 40 may be positioned in the fixed manner as illustrated in FIGS. 4A and 4B or may be positioned so as to be able to perform a scanning operation.

In addition, the probe 40 may include characteristics, such as the element width, the center frequency, and the element arrangement, that are different from those of the scanning probe 30.

(Holding Members 50, 51)

The holding member is a flat plate member for stably maintaining the shape of the subject 21. The holding member can be used as a scanning path of the scanning probe 30. For this reason, the holding member is arranged between the subject and the probe. When the subject is irradiated with light via the holding member, the holding member is a member through which light easily transmits. Additionally, the holding member is a member providing acoustic impedance matching between the living body and the probe. Examples of the material of the holding member include, but are not limited to, a resin material, such as polymethylpentene.

(Signal Collector 70)

The subject information acquisition device of this exemplary embodiment includes the signal collector 70 that amplifies electrical signals acquired by the scanning probe 30 and the probe 40, and converts the electrical signals, i.e., analog signals, into digital signals. The signal collector 70 typically includes an amplifier, an A/D converter, and an FPGA (Field Programmable Gate Array) chip. When a plurality of electrical signals are acquired from the scanning probe 30 and the probe 40, the signal collector 70 can process the plurality of signals simultaneously, which can shorten the time for forming an image.

(Signal Processor 80)

A workstation or the like is typically used as the signal processor 80. Combining detected signals or pieces of image data and image reconstruction are performed by means of software programmed in advance. For example, the software used in the workstation includes two modules, i.e., a combining module 81 configured to combine detected signals or pieces of image data acquired by the scanning probe 30 and the probe 40, and an image reconstruction module 82 configured to generate image data from the detected signals. In photoacoustic tomography, i.e., one kind of photoacoustic imaging, preprocessing, such as noise reduction processing, is performed on signals received at respective positions prior to image reconstruction.

Examples of the algorithm to be used for image reconstruction performed by the image reconstruction module 82 include, but are not limited to, back projection in the time domain or Fourier domain, which is commonly used in the tomography technology. When a large amount of time is allowable for image reconstruction, the image reconstruction method, such as inverse analysis using iteration, can be used.

In addition, in photoacoustic imaging, the use of a focused probe permits an image of the distribution of optical properties inside the living body to be formed without image reconstruction. In such a case, it is not necessary to perform signal processing using the image reconstruction algorithm.

Depending on circumstances, the signal collector 70 and the signal processor 80 are integrally formed. In this case, image information of the subject may be generated by means of hardware processing instead of software processing performed in a workstation.

(Display Device 90)

The display device 90 displays image data output from the signal processor 80. The display method to be used includes a method for displaying MIP (Maximum Intensity Projection) images, slice images, and so forth. In addition, the display device 90 can display a three-dimensional image in multiple different directions, and allows a user to change the tilt and displayed region of a displayed image and the displayed window level and window width while checking the displayed image.

The display device 90 may display a comparison of or difference between image data combined by the signal processor 80 and pieces of image data to be combined by the signal processor 80. Also, the display device 90 can change the emphasis level and the emphasis method of images measured by different probes.

Second Exemplary Embodiment

Figure 5:
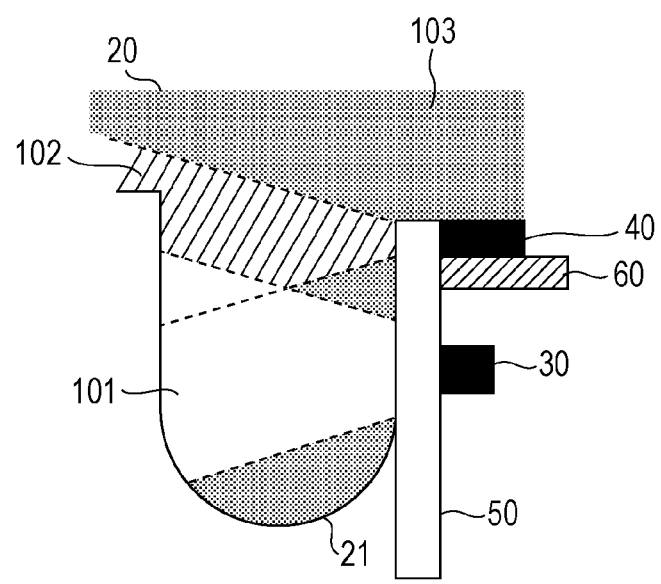
FIG. 5 is a schematic diagram of a subject information acquisition device according to a second exemplary embodiment.

FIG. 5 is a schematic diagram of a subject information acquisition device according to a second exemplary embodiment.

In the subject information acquisition device according to this embodiment, the probe 40 is positioned so that acoustic waves having propagated through the first holding member 50 are detected by the probe 40. That is, the probe 40 is positioned to be in contact with the subject 21 through the first holding member 50. Adopting such a configuration allows the probe 40 to perform scanning along a surface of the first holding member 50 when the probe 40 is of scanning type. In addition, when an acoustic matching material is used as the first holding member 50, acoustic matching can be achieved between the probe 40 and the subject 21. Furthermore, since the probe 40 detects acoustic waves via the first holding member 50 similarly to the scanning probe 30, signals can be combined without delaying the signal. Therefore, the processing time required for combining signals can be shortened.

Third Exemplary Embodiment

Figure 6:
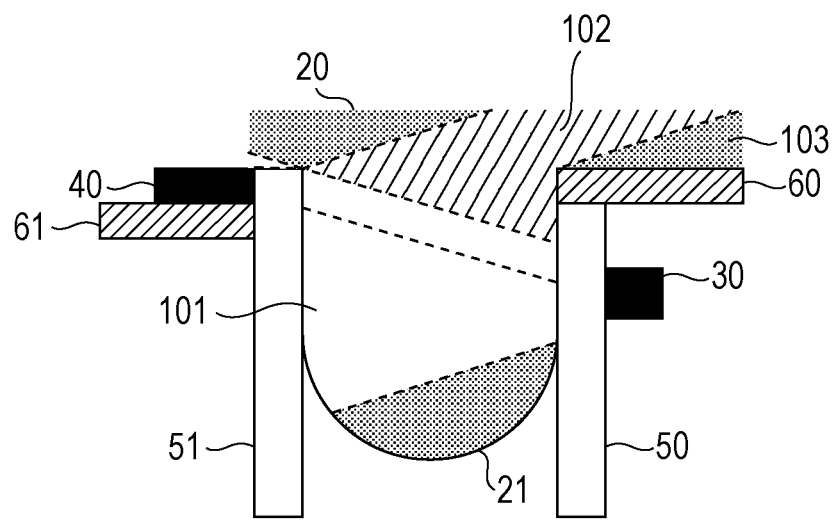
FIG. 6 is a schematic diagram of a subject information acquisition device according to a third exemplary embodiment.

FIG. 6 is a schematic diagram of a subject information acquisition device according to a third exemplary embodiment.

In the subject information acquisition device according to this embodiment, the probe 40 and the scanning probe 30 are positioned so as to face each other, and the probe 40 detects acoustic waves having propagated through the second holding member 51. If the subject 21 can be held only with the first holding member 50, it is not necessary to provide the second holding member 51.

Fourth Exemplary Embodiment

Figure 7:
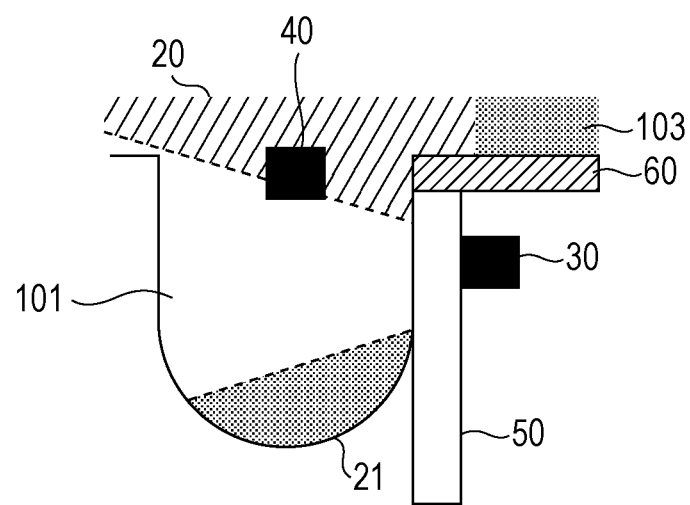
FIG. 7 is a schematic diagram of a subject information acquisition device according to a fourth exemplary embodiment.

FIG. 7 is a schematic diagram of a subject information acquisition device according to a fourth exemplary embodiment.

In the subject information acquisition device according to this embodiment, the probe 40 and the scanning probe 30 are positioned such that a direction perpendicular to the detection surface of the probe 40 is orthogonal to a direction perpendicular to the detection surface of the scanning probe 30. In photoacoustic imaging, a resolution in a direction perpendicular to the detection surface generally differs from a resolution in a direction horizontal to the detection surface. Since a resolution at a part where the detection regions of the scanning probe 30 and the probe 40 overlap is superposition of the resolution in the direction perpendicular to the detection surface of one of the probes and the resolution in the direction horizontal to the detection surface of the other probe, the resulting resolution generally increases.

In addition, the scanning probe 30 and the probe 40 may be positioned so that the directions perpendicular to the detection surfaces of the individual probes cross at an angle other than the right angle.

Fifth Exemplary Embodiment

Figure 8:
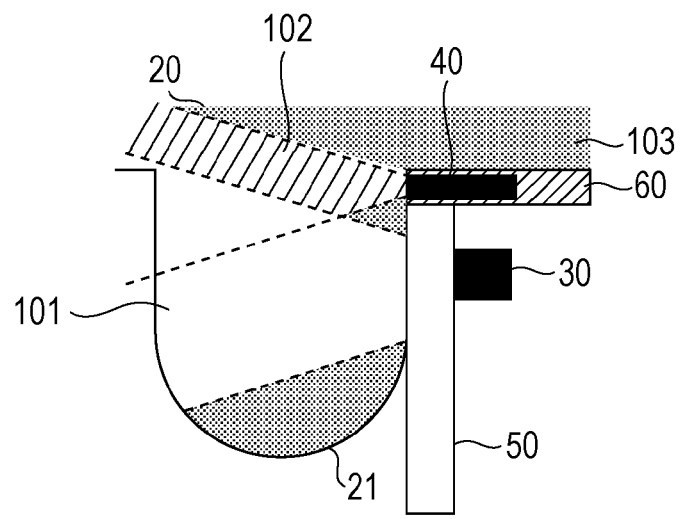
FIG. 8 is a schematic diagram of a subject information acquisition device according to a fifth exemplary embodiment.

FIG. 8 is a schematic diagram of a subject information acquisition device according to a fifth exemplary embodiment.

In the subject information acquisition device according to this embodiment, the probe 40 is positioned so as to at least partially function as the first holding-member support 60.

Figure 9:
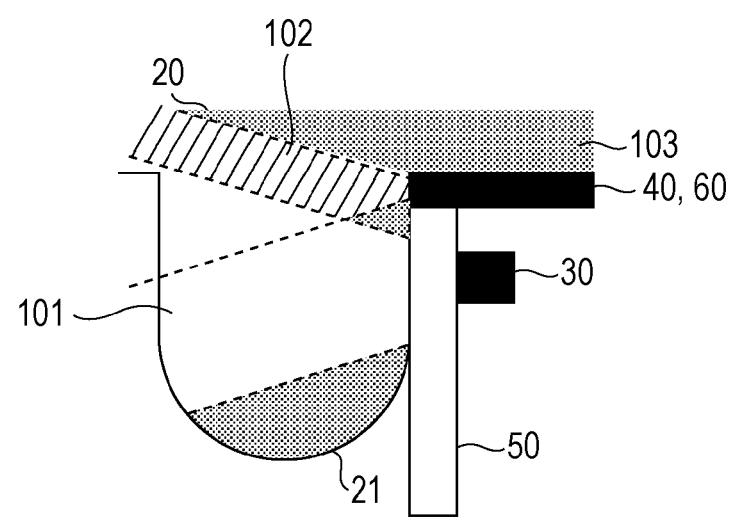
FIG. 9 is another schematic diagram of the subject information acquisition device according to the fifth exemplary embodiment.
Figure 10:
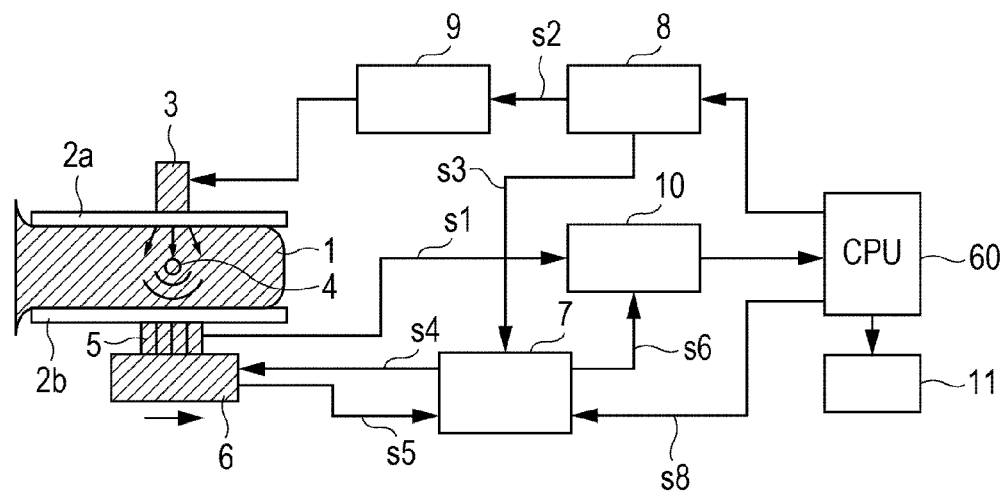
FIG. 10 is a diagram illustrating a configuration of a measuring device according to the related art described in PTL 1.

The probe 40 does not have to be entirely surrounded by another member, and instead, part of the probe 40 may be exposed from the other member. Furthermore, for example as illustrated in FIG. 9, the probe 40 may have a function of the first holding-member support 60. However, when the probe 40 has a function of another member in this manner, a housing of the probe 40 has to be designed to be suitable as the other member.

In addition, the probe 40 may be positioned so as to at least partially function as any of the first holding member 50, the first holding-member support 60, the second holding member 51, the second holding-member support 61, and the patient support 63.

While exemplary embodiments have been described above, aspects of the present invention are not limited to these embodiments and encompass various modifications and applications as long as the modifications and applications do not depart from the scope of the claims. Additionally, aspects of the present invention are applicable not only to photoacoustic imaging but also to other kinds of imaging using acoustic waves.

According to the subject information acquisition device as described above, the shape of a subject may be stably maintained and high-quality images may be acquired.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Patent Application No. PCT/JP2011/072577, filed Sep. 30, 2011, which is hereby incorporated by reference herein in its entirety.

The invention claimed is:

1. A photoacoustic imaging device comprising:
 a patient support member having an upper support surface and configured to support a patient in a prone position;
 a pair of holding plates, each plate having a holding surface so as to sandwich a breast of the patient therebetween;
 a movable probe located on one plate of the pair of holding plates in opposition to a corresponding holding surface of an other plate of the pair of holding plates, the movable probe being configured to be movable along the one plate of the pair of holding plates and configured to detect an acoustic wave generated at a first region of the breast and propagated through the one plate of the pair of holding plates;
 a scanning mechanism configured to move the movable probe along the one plate of the pair of holding plates so as to change a distance between the patient and the movable probe;
 a holding plate support located beneath the patient support member and configured to support the one plate of the pair of holding plates; and
 a stationary probe provided to detect an acoustic wave generated at a second region of the breast,
 wherein the holding plate support is located closer to the patient support member than the movable probe so as to restrict an upper scanning region of the movable probe, and
 wherein the stationary probe is located between the patient support member and the holding plate support such that the second region of the breast is located closer to the patient support member than the first region.

2. The photoacoustic imaging device according to claim 1, wherein the stationary probe is located closer to the patient support member than the movable probe so as to detect the acoustic wave generated at the second region of the breast not through the one plate of pair of holding plates.

3. The photoacoustic imaging device according to claim 1, wherein the stationary probe is located so as to face the movable probe and to detect the acoustic wave generated in the second region of the breast and propagated through the other plate of the pair of holding plates.

4. The photoacoustic imaging device according to claim 2, wherein the stationary probe is located so as to detect the acoustic wave generated in the second region of the breast and propagated through the one plate of the pair of holding plates.

5. The photoacoustic imaging device according to claim 1, wherein the stationary probe is fixed with respect to the breast.

6. The photoacoustic imaging device according to claim 1, further comprising a signal processing unit configured to generate a first image data based on a signal detected by the movable probe, generate a second image data based on a signal detected by the stationary probe, and to generate combined image data of the first image data and the second image data.

7. The photoacoustic imaging device according to claim 1, wherein the stationary probe includes an array of transducers arranged along a distant direction which a distance from the patient support member has a different value.

8. The photoacoustic imaging device according to claim 7, wherein
the stationary probe is configured to select some of the transducers to operate among the array of transducers.

9. The photoacoustic imaging device according to claim 6, wherein
a center frequency of the movable probe is different from a center frequency of the stationary probe, and
the signal processing unit is configured to match a resolution of the first image data and a resolution of the second image data and to generate the combined image data after matching the resolution of the first image data and the resolution of the second image data.

10. The photoacoustic imaging device according to claim 6, wherein the signal processing unit is configured to cause a display device to display a comparison between the combined image data, the first image data, and the second image data.

11. The photoacoustic imaging device according to claim 1, further comprising a signal processing unit configured to generate a combined signal of a signal detected by the movable probe and a signal detected by the stationary probe and generate image data based on the combined signal.

12. The photoacoustic imaging device according to claim 1, wherein the one plate of the pair of holding plates is located between the movable probe and the breast, and the stationary probe is in direct contact with the breast.

13. A photoacoustic imaging apparatus comprising:
a first holding plate;
a second holding plate located so as to face the first holding plate and configured to interpose a breast of a patient with the first holding plate;
a movable probe configured to detect an acoustic wave generated at a first region of the breast and propagated through the first holding plate;
a scanning mechanism configured to move the movable probe in a scanning range along the first holding plate to scan the first region of the breast;
a first holding-plate support configured to maintain the first holding plate at a patient side and to limit the scanning range of the movable probe; and
a stationary probe located at a fixed position on the patient side between the patient and the first holding-plate support out of the scanning range of the movable probe, the stationary probe configured to detect an acoustic wave generated at a second region of the breast, the second region is located closer to the patient side than the first region.

* * * * *